(12) United States Patent
Addis

(10) Patent No.: US 6,251,119 B1
(45) Date of Patent: Jun. 26, 2001

(54) DIRECT STICK TEAR-AWAY INTRODUCER AND METHODS OF USE

(75) Inventor: Bruce Addis, Redwood City, CA (US)

(73) Assignee: Embol-X, Inc., Mountain View, CA (US)

( * ) Notice: Subject to any disclaimer, the term of this patent is extended or adjusted under 35 U.S.C. 154(b) by 0 days.

(21) Appl. No.: 09/131,181

(22) Filed: Aug. 7, 1998

(51) Int. Cl.[7] ........................................ A61B 17/32
(52) U.S. Cl. .................. 606/167; 604/96.01; 604/160; 128/898
(58) Field of Search .................... 606/167, 170; 604/160, 96.01; 128/898

(56) References Cited

U.S. PATENT DOCUMENTS

| | | | |
|---|---|---|---|
| 3,651,807 | * 3/1972 | Huggins | 606/108 |
| 5,114,401 | * 5/1992 | Stuart et al. | 604/161 |
| 5,167,634 | * 12/1992 | Corrigan et al. | 604/161 |
| 5,318,542 | * 6/1994 | Hirsch et al. | 604/161 |
| 5,951,518 | * 9/1999 | Licata et al. | 604/161 |

* cited by examiner

*Primary Examiner*—Glenn K. Dawson
(74) *Attorney, Agent, or Firm*—Lyon & Lyon LLP

(57) ABSTRACT

A direct stick tear-away introducer having an elongate intraluminal medical device, comprising a proximal and a distal end. A sheath is disposed about the medical device and extends from the distal end of the medical device. A blade is bonded to a distal end of the sheath, and a weakened region on the sheath extends longitudinally from the distal end to a proximal end of the sheath. The introducer has the ability to incise a body tissue and allow insertion of a medical device housed within the introducer into the body tissue. Methods for using the devices herein are also disclosed.

4 Claims, 2 Drawing Sheets

DIRECT STICK TEAR-AWAY INTRODUCER AND METHODS OF USE

FIELD OF THE INVENTION

The present invention relates generally to inserting an introducer into a body tissue or cavity, including a patient's vascular system, and more particularly, to an introducer which provides access for medical devices, such as infusion catheters, pressure monitors, filters, balloon occluders, and/or cardioplegia catheters.

BACKGROUND OF THE INVENTION

A cannula is commonly used to introduce a catheter into a body cavity, such as a blood vessel. After the catheter has been inserted into the body cavity, the cannula, if left in place, may interfere with a surgical field. Removal of the cannula, therefore, is often desired. However, it is sometimes difficult to remove the cannula due to frequently enlarged proximal end of the catheter. This problem has been alleviated by splitable cannulas, which can be removed from a patient's blood vessel by separating into two parts, as described in U.S. Pat. Nos. 4,865,593, 5,104,388, and 5,318, 542, all of which are incorporated herein by reference. Although the disclosed splitable cannulas are easy to remove, they all require an access mechanism to incise the blood vessel for insertion. Moreover, a distal end of a catheter, housed within the splitable cannula, often protrudes from the distal end of the cannula, and thus can be damaged by sometime calcific plaque of the blood vessel walls.

A need, therefore, exists for a cannula system which provides easy access, protection, and insertion of a medical device into a body tissue, and is removable by sliding.

SUMMARY OF THE INVENTION

The present invention provides a cannula system having the ability to incise a body tissue and allow insertion of a medical device housed within the cannula into the body tissue. The cannula system is a direct stick tear-away introducer which comprises an elongate intraluminal medical device having a proximal and a distal end. A sheath is disposed about the medical device and extends from the distal end of the medical device. A retractable blade is bonded to a distal end of the sheath, and a weakened region on the sheath extends longitudinally from the distal end to a proximal end of the sheath. The proximal end of the sheath may include a handle. The weakened region of the sheath may be a line of perforation. The sheath can be made from plastic, polycarbonate, or other suitable materials. The blade at the distal end of the sheath can be made of stainless steel, nitinol, or other suitable material. The blade may further have a lubricious coating with split to facilitate tear-away action. The sheath may extend from the distal end to the proximal end of the medical device. The medical device, therefore, is protected from damage during insertion.

The present invention also provides methods for introducing a medical device, including infusion catheters or cannulas, pressure monitors, balloon occluders, filters, or aspirators into a body tissue by providing a tear-away sheath, which is disposed about the medical device, and has a weakened region extending longitudinally and a blade bonded to its distal end. An incision in the body tissue is made using the blade bonded to the distal end of the sheath. The medical device is advanced into the body tissue through the incision, and the sheath and blade are removed by separating the sheath along its weakened region. In an alternative embodiment where the proximal end of a direct stick tear-away introducer has a handle, the sheath and blade can be removed by pulling on the handle. In this way, a medical device is introduced into a body tissue by the direct stick tear-away introducer, which can be easily removed and obviates the need for an access mechanism.

DETAILED DESCRIPTION OF THE PREFERRED EMBODIMENTS

Figure 1:
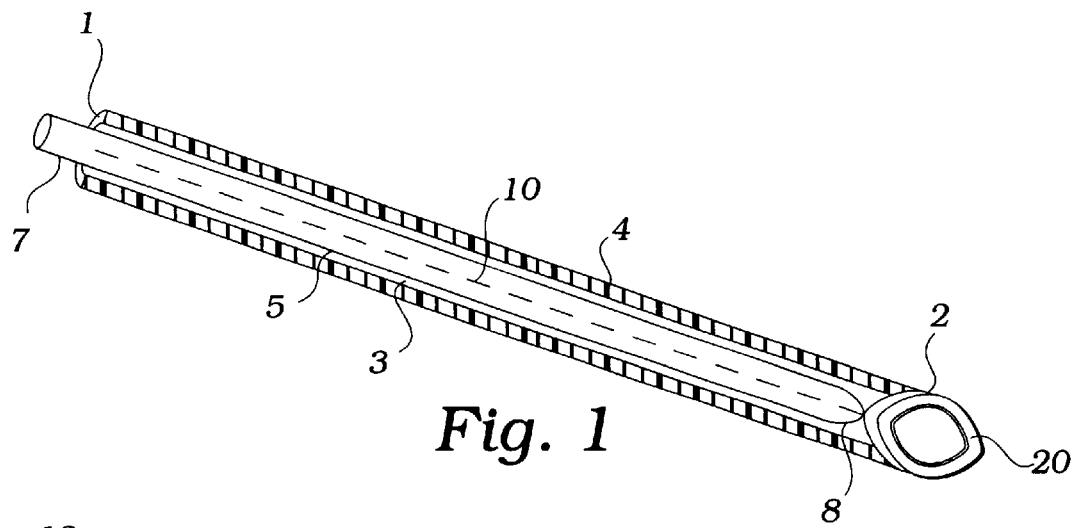
FIG. 1 depicts a preferred embodiment of a direct stick tear-away introducer carrying a catheter in its lumen.

The devices and methods disclosed herein can be used for deployment of various medical devices, including infusion catheters, aspirators, balloon occluders, filters, and cardioplegia catheters into a body tissue or cavity. FIG. 1 depicts a preferred embodiment of a direct stick tear-away introducer carrying a cannula in its lumen. Cannula 5 has proximal end 7 and distal end 8 which is housed within introducer lumen 3. The introducer has perforation 10 on sheath 4 extending longitudinally from proximal end 1 to distal end 2. Retractable blade 20 is bonded on the distal end of the sheath.

Figure 2:
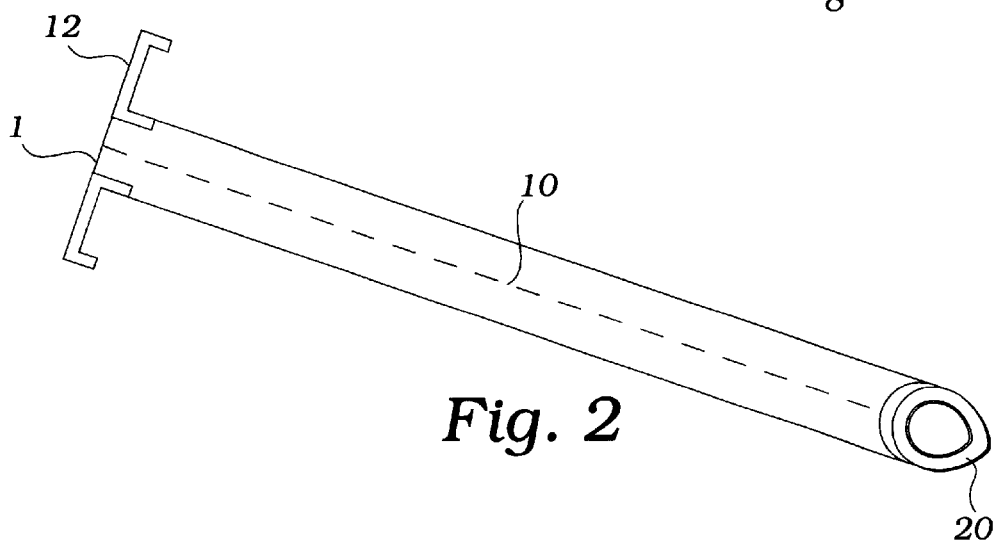
FIG. 2 depicts an alternative embodiment of a direct stick tear-away introducer having a handle at its proximal end.

FIG. 2 depicts an alternative embodiment of a direct stick tear-away introducer having handle 12 at proximal end 1. The handle may facilitate separation of the introducer sheath along perforation line 10.

Figure 3:
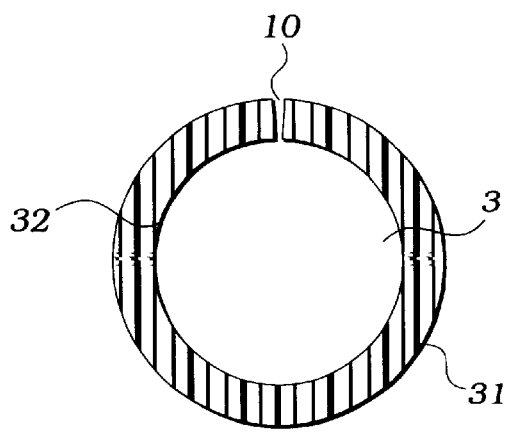
FIG. 3 depicts a cross-sectional view of a direct stick tear-away introducer at a perforating point.
Figure 4:
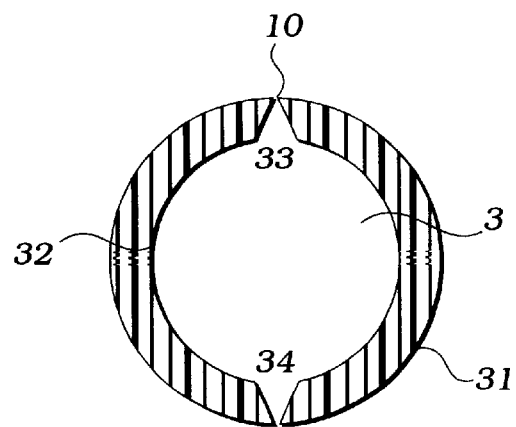
FIG. 4 depicts a cross-sectional view of an alternative of a direct stick tear-away introducer having multiple lines of perforation.

FIGS. 3 and 4 depict a cross-sectional view of a direct stick tear-away introducer at a perforating point. The introducer has outer layer 31 and inner layer 32. The inner and outer layers of the introducer are continuous at perforation 10. In FIG. 4, two longitudinal wedges 33 and 34 penetrate the inner layers. Other geometric cuts in the inner layers are also possible to provide easy tear-away of the introducer sheath.

The length of a direct stick tear-away introducer is generally between 5 and 30 centimeters, preferably approximately 15 centimeters. The outside diameter of the introducer is generally between 0.5 and 2.0 centimeters, preferably approximately 1.5 centimeters. The foregoing ranges are set forth solely for the purpose of illustrating typical device dimensions. The actual dimensions of a device constructed according to the principles of the present invention may obviously vary outside of the listed ranges without departing from those basic principles.

Figure 5:
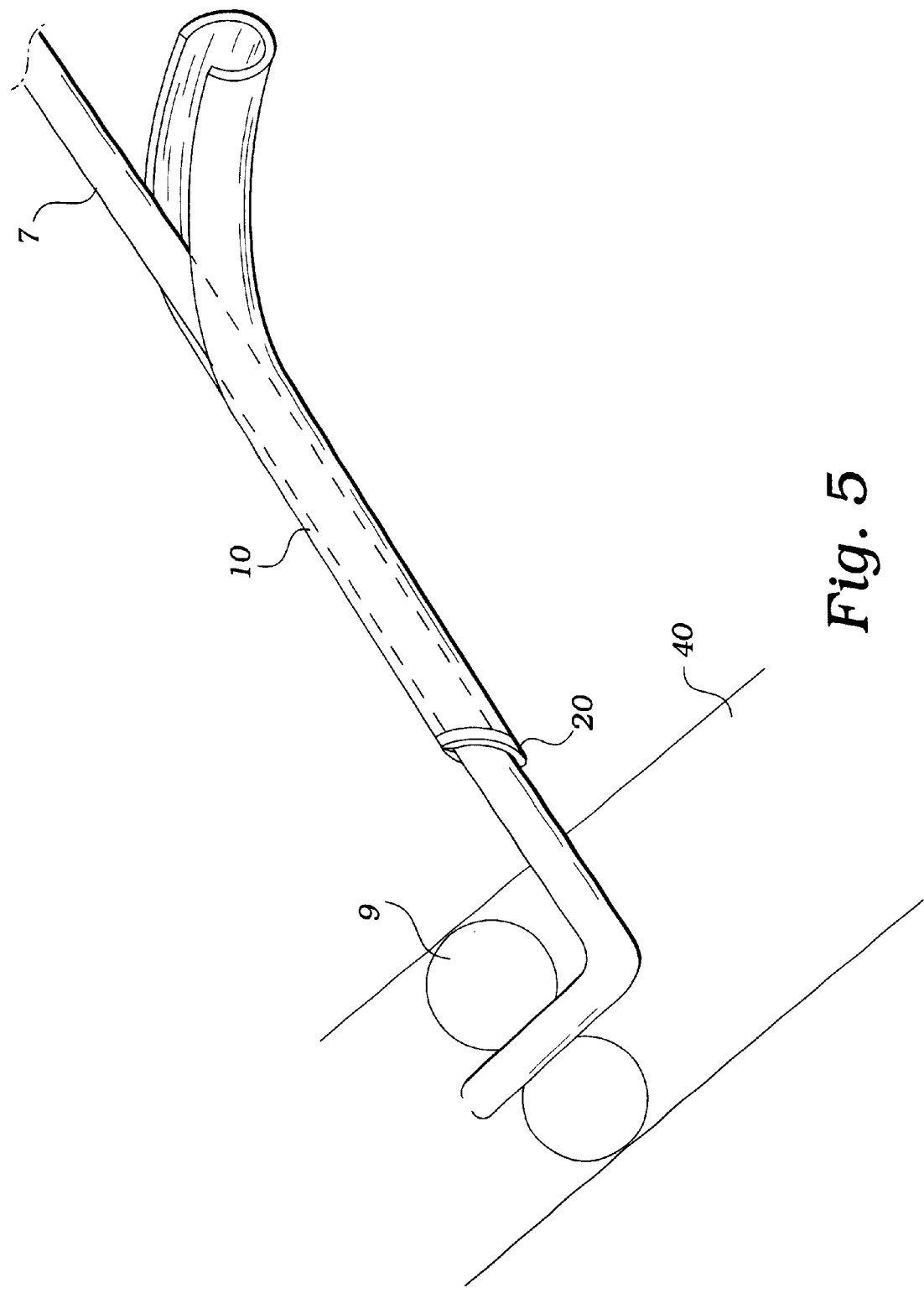
FIG. 5 depicts a cannula having a balloon occluder deployed into an aorta using a direct stick tear-away introducer.

FIG. 5 depicts a cannula deployed in an aorta using a direct stick tear-away introducer. The cannula has balloon occluder 9 mounted at its distal end. After an incision is made in aorta 40 by retractable blade 20, the introducer, housing the cannula, is inserted into the aorta. In this way, the cannula and especially the balloon occluder are protected from puncture by the sometimes-calcific plaque of the aortic walls. The cannula is then advanced distally into the aorta, and the balloon occluder is inflated to occlude the aortic lumen. The introducer may be withdrawn outside the aorta and removed by separating its sheath along perforation 10.

Methods disclosed herein can be used for cannulation of any body tissue, and are particularly useful in deployment of an arterial cannula in minimally invasive coronary artery bypass grafting surgery for delivering oxygenated blood from a cardiopulmonary bypass machine and for occluding the aortic lumen to provide arterial isolation of heart and coronary blood vessels from the peripheral vascular system. In a port-access approach (see Reichenspumer et al., *Annals of Thoracic Surgery* 65:413–419 (1998), incorporated herein by reference) after a patient is under general anesthesia, a small incision is made in the intercostal space for insertion of the cannula. The direct stick tear-away introducer housing the arterial cannula can be inserted through the access port, and the sheath and blade are removed by separating the sheath along its weakened region. Therefore, methods disclosed herein provide a time-efficient way for aortic cannula especially in minimally invasive surgery.

Although the foregoing invention has, for the purposes of clarity and understanding, been described in some detail by way of illustration and example, it will be obvious that certain changes and modifications may be practiced which will still fall within the scope of the appended claims.

What is claimed is:

1. A method for introducing a balloon cannula into the aorta, comprising the steps of:

providing a tear-away sheath-sheath disposed about the balloon cannula, the sheath having a weakened region extending longitudinally and a blade bonded to a distal end of the sheath;

making an incision in the aorta using the blade bonded to the sheath;

advancing the balloon cannula into the aorta through the incision; and removing the sheath and blade from the aorta by separating the sheath along its weakened region.

2. The method of claim 1, wherein the tear-away sheath further comprises a handle attached to a proximal end thereof.

3. The method of claim 2, wherein the step of removing the sheath and blade further comprises the step of pulling proximally on the handle.

4. The method of claim 1, further comprising the step of inflating a balloon of the balloon cannula inside the aorta.

* * * * *